United States Patent [19]

Jen Wu et al.

[11] Patent Number: 5,589,685

[45] Date of Patent: Dec. 31, 1996

[54] MATRIX ENHANCED SIMS

[76] Inventors: Kuang Jen Wu, 2705 Alma St.; Robert W. Odom, 2068 Harvard St., both of Palo Alto, Calif. 94306

[21] Appl. No.: 451,257

[22] Filed: May 26, 1995

[51] Int. Cl.⁶ .................................................. H01J 49/90
[52] U.S. Cl. ............................ 250/282; 250/288
[58] Field of Search ................... 250/288, 288 A, 250/282, 281, 287

[56] References Cited

U.S. PATENT DOCUMENTS

| | | | |
|---|---|---|---|
| 4,719,349 | 1/1988 | Phillips et al. | 250/288 |
| 4,920,264 | 4/1990 | Becker | 250/282 |
| 4,988,879 | 1/1991 | Zare | 250/423 |
| 5,062,935 | 11/1991 | Schlag et al. | 204/157.41 |
| 5,118,937 | 6/1992 | Hillenkamp et al. | 250/282 |
| 5,171,989 | 12/1992 | Williams et al. | 250/288 |
| 5,210,412 | 5/1993 | Levis et al. | 250/288 |
| 5,221,841 | 6/1993 | Nagai et al. | 250/251 |
| 5,245,185 | 9/1993 | Busch et al. | 250/288 |
| 5,285,064 | 2/1994 | Willoughby | 250/288 |
| 5,288,644 | 2/1994 | Beavis et al. | 436/94 |
| 5,382,793 | 1/1995 | Weinberger et al. | 250/288 |

*Primary Examiner*—Jack I. Berman
*Assistant Examiner*—Kiet T. Nguyen
*Attorney, Agent, or Firm*—Robert S. Smith

[57] ABSTRACT

In a mass spectroscopy method, a primary beam of energetic particles is irradiated onto a target surface containing a sample in which the sample is a collection of analyte molecules contained in a matrix forming compound. When it is required to eject positive analyte ions the matrix forming compound can be a proton donor. When it is required to eject a negative analyte ion, the matrix forming compound can be a proton acceptor.

25 Claims, 4 Drawing Sheets

MATRIX ENHANCED SIMS

FIELD OF THE INVENTION

This invention relates to mass spectrometry methods and particularly to methods for preparing and analyzing samples using mass spectrometzic techniques.

PRIOR ART AND INFORMATION DISCLOSURE STATEMENT

Mass Spectrometry is a general method of determining the mass of elements, inorganic and organic molecules as well as fragments of these molecules by forming ions from these neutral species and determining the mass-to-charge ratio of these ions using various techniques including ion (charged particle) momentum, energy or velocity analysis as well as resonance frequencies in crossed electromagnetic fields. Measurement of both ion mass and ion intensity forms the basis of quantitative analysis by mass spectrometry. Time of flight mass spectrometry (TOFMS) typically performs mass analysis by forming ions in short pulses, accelerating the packets of ions through an electric field to a fixed kinetic energy and measuring the transit time or time-of-flight of the ions between their formation point and an ion detector located some distance (ranging between tens of centimeters to several meters) from the ion formation point. Since the ion velocity is inversely proportional to the ion mass, the ion arrival time spectrum can be converted into a mass spectrum using appropriate mass calibration.

TOFMS has been particularly effective in measuring the mass of all ions formed in the ionization event since the technique measures ion flight times and hence does not require scanning techniques to develop the mass spectrum. In additions, TOFMS can readily measure high mass ions (masses greater than several thousand atomic mass units or Daltons (Da)) since ion detection is based solely on measuring ion flight times. Methods of producing high mass ions from inorganic or organic molecules in TOFMS analyses include using energetic, pulsed beams of particles (charged or uncharged) or photons which strike the surface of a solid or a liquid. These pulsed beams (primary beams) sputter atoms and molecules from the surface and a fraction of the sputtered material is ionized. Primary beams have included electron, photon, ion and neutral atoms or molecules.

For example, U.S. Pat. No. 4,920,264, to Becker discloses a method for the processing and preparation of a sample of one or more nonvolatile or thermally labile molecules dissolved in a solvent, freezing the solution and exposing the frozen solution to a source of energy to desorb the molecules to be analyzed from the surface of the frozen solution. The method does not disclose any critria for selecting the matrix forming compound selected in combination with the desorbing beam to augment rate of ejection of the analyte ions.

U.S. Pat. No. 4,988,879 to Zare et al discloses a method of causing a layer of analyte molecules to be physisorbed onto an inert support surface, desorbing molecules of the layer using a desorption laser and ionizing the desorbed molecules with an ionization laser.

U.S. Pat. No. 5,062,935 to Schlag et al discloses sample preparation for TOFMS by mixing the sample substance with a matrix forming compound. The matrix forming compound is selected to be "easily decomposed" by laser beam pulses such that the matrix surrounding the sample molecule are removed and the sample molecule is ejected from the surface of the molecule without fractionation. Examples of the Schlag invention include addition of a peptide to an aqueous solution of sugar which is dried prior to further analysis, mixing peptide with polyethylene powder, and mixing peptide with polyethylene and metal powders. This technique was shown to be successful in suppressing fragmentation of the sample molecules.

U.S. Pat. No. 5,118,937 to Hillenkamp et al discloses laser desorption of analyte molecular ions using laser light of a wavelength of about 300 nm or greater and using a matrix which is able to absorb in this wavelength range. Most biomolecules do not absorb in this range so that desorption of intact sample molecules is possible.

U.S. Pat. No. 5,171,989 to Williams et al discloses the method of providing sample molecules in an aqueous solution containing one or more organic solvents, introducing the mixture into a vacuum through a capillary such that, ice containing the organic solvent as well as the sample molecule is formed on the tip of the capillary.

The ice is energized with a primary beam such as to volatilize the sample molecules. The improvement of the invention is the introduction of the organic solvent to stabilize the formation of the ice.

U.S. Pat. No. 5,245,185 to Busch et al discloses a method and apparatus for releasing analyte molecules mixed in a gel from an electrophoretogram and disposing them for analysis by TOFMS.

U.S. Pat. No. 5,285,064 to Willoughby discloses nebulizing an effluent from a process stream by combined thermal and pneumatic processes within a heated cylinder to form a collimated desolvated aerosol capillary tube. The enriched particles are vaporized, ionized and detected by particle detectors.

U.S. Pat. No. 5,288,644 to Beavis discloses a method for DNA sequencing in which the molecular weights of DNA fragments having a common origin are detected by a matrix assisted laser desorption mass spectrometry. Sample preparation is achieved by adding one microliter of sample solution to 5–10 microliters of matrix solution. When a spot of the mixture is placed on a specimen disk and dried, a solid solution of sample and one thousand fold matrix is ready for desorption by photons.

U.S. Pat. No. 5,382,793 to Weinberger et al discloses a liquid desorption ionization mass spectrometer including a sample lock for introducing probes from whose tip crystallized samples of analyte and matrix are laser desorbed.

All of the techniques for sample preparation disclosed in the cited an are directed toward matrix assisted laser desorption ionization (MALDI). The approach is to select a combination photon wavelength and matrix compound wherein the matrix absorbs the radiation of the desorbing laser in order to provide localized energy that assists in the ejection of the analyte molecule. This method is intended to minimize fragmentation of the analyte molecule. Due to MALDI's highly destructive nature and gas phase transition processes, mass measurement accuracy in MALDI is limited to a maximum of 0.01% when analysis is performed on state of the art TOFMS instruments. MALDI techniques also place limitations on mass resolution where isotropic distribution of the analyte are not readily resolved.

The literature also discloses the use of primary beams of ions and neutral particles, fast atom bombardment (FAB). In which analyte molecules are dispersed in a liquid. The liquid/analyte mixture is subsequently bombarded with an energetic beam of atoms, neutral molecules, or ions and the ionization produced by this primary particle/liquid interaction is analyzed by mass spectrometry techniques.

For example, U.S. Pat. No. 4,719,349 to Phillips et al discloses a dual electrode sample probe having a target surface on which is deposited a liquid sample for bombardment by neutral particles or ions to produce secondary (analyte) ions.

U.S. Pat. No. 4,920,264 discloses the method of dissolving the analyte in a low molecular weight solvent, freezing the solution on a target surface and desorbing the analyte molecule using a primary beam such as a laser, electron, neutral particle or ion beam.

U.S. Pat. 5,221,841 t Nagai et al discloses a fast atom beam source including a an ion source that emits an ion beam and an electron gun that emits an electron beam at a speed substantially equal to the speed of the ions and coincident with the ions.

Although these references disclose the analyte molecules being dispersed in a matrix, there is no indication as to how the matrix compound is selected in order to optimize rate of ejection.

A method for analyzing spatial (lateral) distribution of ions in a large molecue includes rastering a large diameter primary ion beams and transporting an image of the analyte ions produced at a surface through the mass analysis region. Typical primary beam diameters range from tens of micrometers to several mm and image resolutions approach 1–5 micrometer in this ion microscope technique. An ongoing interest is to find techniques which improve resolution of the ion microscope. Another method for determining the lateral distribution of ions of large molecules utilizes a microfocused, energetic primary beam which is rastered over a solid surface. Analyte ions formed in this microprobe technique in which the primary beam is 0.1 to 10 micrometers in diameter are analyzed by mass spectrometry techniques.

OBJECTS

It is an object of this invention to overcome the limitations on resolution and precision of measuring molecular mass using TOFMS that are imposed by the use of matrix assisted laser desorption ionization (MALDI). Specifically, this object includes:

1. eliminating the need for a laser,
2. not requiting a matrix that is matched to a laser wavelength to absorb energy,
3. enlarging the selection of the matrix forming compounds to accommodate other requirements such as minimizing destruction of the submonolayers of the sample substrate;
4. improving control over desorption and ionization mechanisms;
5. minimizing destruction of the analyte/matrix mixture to within the neat surface (top few monolayers).

It is another object to determine the spatial distribution of analyte molecules in solid materials at lateral resolutions (0.1 to 5 micrometer) which are unachievable by either MALDI or fast atom bombardment (FAB).

It is another object of this invention to overcome the limitations on resolution and precision of measuring molecular mass using TOFMS that are imposed by the use of FAB.

Specifically, this object includes energetic particle bombarding a solid matrix absent a solvent resulting in:

1. less fragmentation of the analyte molecule;
2. low matrix-analyte interaction;
3. greater tolerance to the presence of salt and impurities;

It is another object to determine the spatial distribution of analyte molecules in solid materials at lateral resolutions (~1 micrometer) unachievable by either MALDI or FAB techniques.

SUMMARY

This invention is directed toward a matrix-enhanced ejection of analyte particulates which are understood by those skilled in the art to mean clumps of one or more molecules by directing a sputtering beam of primary energetic particles (charged or neutral) against analyte molecules combined with an appropriate matrix forming compound.

In the context of this specification, the term "matrix-enhanced-secondary-ion-mass spectrometry (ME-SIMS) will be understood to mean the method of this invention in which a primary energetic beam irradiates a sample composed of analyte molecules mixed with a matrix forming compound especially selected such that the ionization efficiency of analyte ions from the sample is enhanced In accordance with this invention, matrix forming compounds are selected as proton donors in order to promote the ionization and ejecting positive analyte ions. Matrix forming compounds are selected as proton acceptors in order to promote the ionization and ejection of negative analyte ions. Analyte ion ejection efficiencies have been observed to increase by a factor as great as 10,000 using matrix forming compounds such as those described below.

The method is particularly effective in measuring molecular weights of analyte molecules up to 20,000 Daltons mixed in a matrix of molecules having molecular weights between 100 and 1000 Da. While we do not wish to be bound by theory, it is believed that the improved mass resolution and mass measurement accuracy resulting from the practice of this invention results from mechanisms of release of the ejected analyte ions which are different from those operative in the techniques of the present state of the art. These release mechanisms resulting from primary particle energy deposited in the solid mixture causing sputtering of analyte and matrix molecules include:

1. Binary collisions of primary particle and/or analyte molecules causing recoil ejection of these molecules from the surface;
2. Formation of microshock waves in the solid induced by the primary particle with the analyte and matrix molecules in the solid leading to ejection of analyte or matrix molecules from near the surface of the solid (10 nm depth).
3. Multiple quasi—elastic collisions (collision cascade) of primary particle with analyte and matrix molecules in the solid leading to ejection of analyte or matrix molecules from the near surface (to a depth of 10 nm) of the solid.

Producing the ejection and ionization of the analyte by a carefully controlled sputtering process provides a small kinetic energy distribution of the ejected analyte molecules leading to improved mass resolution and precision of the method of this invention as reported in the following Description of the Preferred Embodiments.

Processes by which it is believed that ionization of the analyte molecule can occur include:

1. Electronic transitions occurring in the primary particle/analyte or matrix molecule collisions;
2. Charge transfer (transfer of $H^+$, $H^-$, beta particles) between the analyte and matrix, analyte and primary particle or matrix and primary particle;

3. Transfer of charged atom or molecule or molecular fragment from matrix to analyte molecules;

4. Electron tunneling processes occurring between the sputtered analyte and/or matrix molecules and the non-sputtered solid surface.

DESCRIPTION OF PREFERRED EMBODIMENTS

Figure 1:
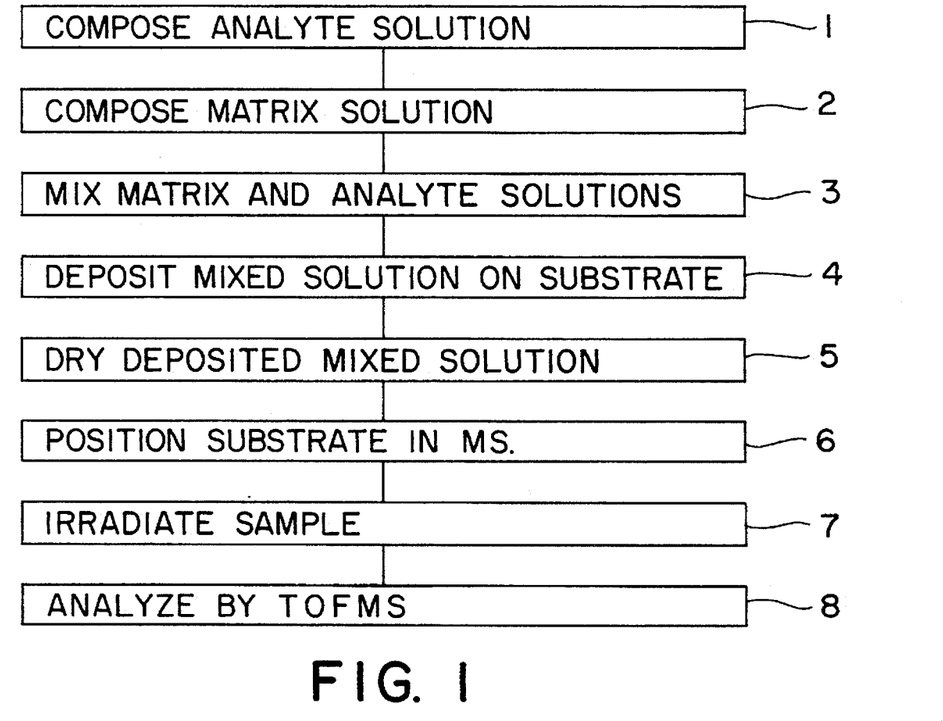
FIG. 1 is a flow diagram of the method of this invention.

Turning now to a detailed discussion of embodiments of the invention, FIG. 1 lists the steps for performing the method of this invention:

Step 1. Dissolve analyte in organic or inorganic solvent to produce an Analyte Solution. Possible selections of a solvent that may be considered, depending on the situation, may include water, acetonitrile, alcohol, acetone, acid, bensene, ether, chloroform, pyridine, and aqueous alkaline solutions.

Step 2. Select a matrix forming compound that enhances ionization efficiency of the analyte ion.

Step 3. Dissolve the matrix forming compound in an organic or inorganic solvent to produce a Matrix Solution.

Step 4. Mix Analyte and Matrix solutions with Analyte to Matrix molecular concentration ratios ranging between 1 to $10^{-5}$.

Step 5. Deposit small volume (e.g., 1 microliter) of combined solutions on a solid substrate such as silicon, stainless steel or silver foil; Alternative substrates may be other metals, semiconductors or insulators as the situation requires.

Step 6. Dry solutions in air or vacuum which converts the solution to a solid crystalline or amorphous residue.

Step 7. Insert solid residue on the substrate into the sample region of a mass spectrometer.

Step 8. Irradiate the sample with an energetic beam of particles (positive or negative ions, electrons or positrons, neutral particles). The species of ion is selected from a group of ions that includes $^{69}Ga^+$, $Cs^+$, $O_2^+$, cluster ion beams, for example, $Au_x^+$ beams of molecular species, noble gas ions such as $Ar^+$, $Xe^+$, $Kr^+$. Impact energies can range from several hundred electron volts to several million electron volts and total radiation doses can range from a few thousand to greater than $10^{15}$ particles/cm$^2$.

Step 9. Analyze by mass spectrometry techniques, the mass-to-charge ratio of the positive or negative ions produced in the energetic particle/solid residue interaction. Equivalently, a small volume of matrix solution can be deposited directly on a solid substrate containing the analyte and steps 6 through 9 are performed.

Figure 2:
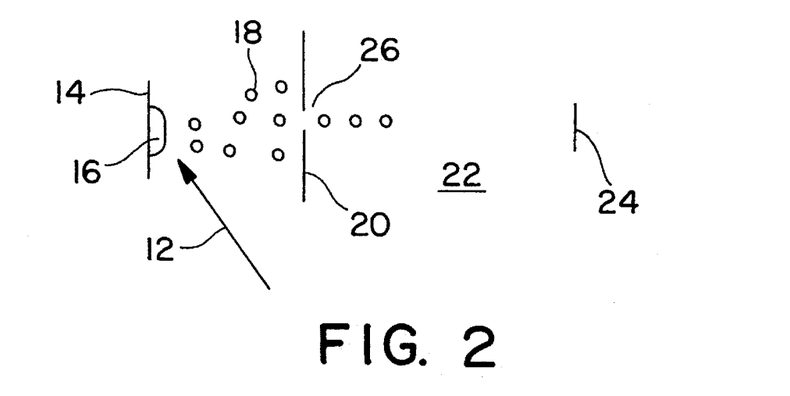
FIG. 2 shows the arrangement of the mass spectrometer.

FIG. 2 shows the mass spectrometry system for analyzing the mass-to-charge ratio according to step 8 in which a mass spectrometer 10 has a primary beam 12 radiating a substrate 14 on which is deposited a matrix-analyte sample 16 as discussed above. Ejected ions 18 are subjected to an extraction voltage applied between substrate 14 and an accelerating electrode 20 and are projected through aperture 26 into drift region 22 toward planar detector 24. Rate of arrival at the detector vs. drift time of analyte particulates is measured. According to a preferred embodiment, the primary particle beam 12

1. has a pulse length range, <2 nanosecond,
2. has a pulse repetition rate ranging between 100 and 100,000 Hz,
3. has a maximum primary ion dose—$10^{15}$ ions per cm$^2$ The accelerating voltage applies an ion extraction field greater than 1 volt per micrometer between substrate 14 and an accelerating electrode 20.

Under these conditions two species of analyte ions having a small difference in molecular weight such as molecules containing isotopes are distinguished from one another by two peaks in the signal received by planar detector 24. A high speed time-to-digital converter (TDC) is used which resolves the peaks.

Figure 3:
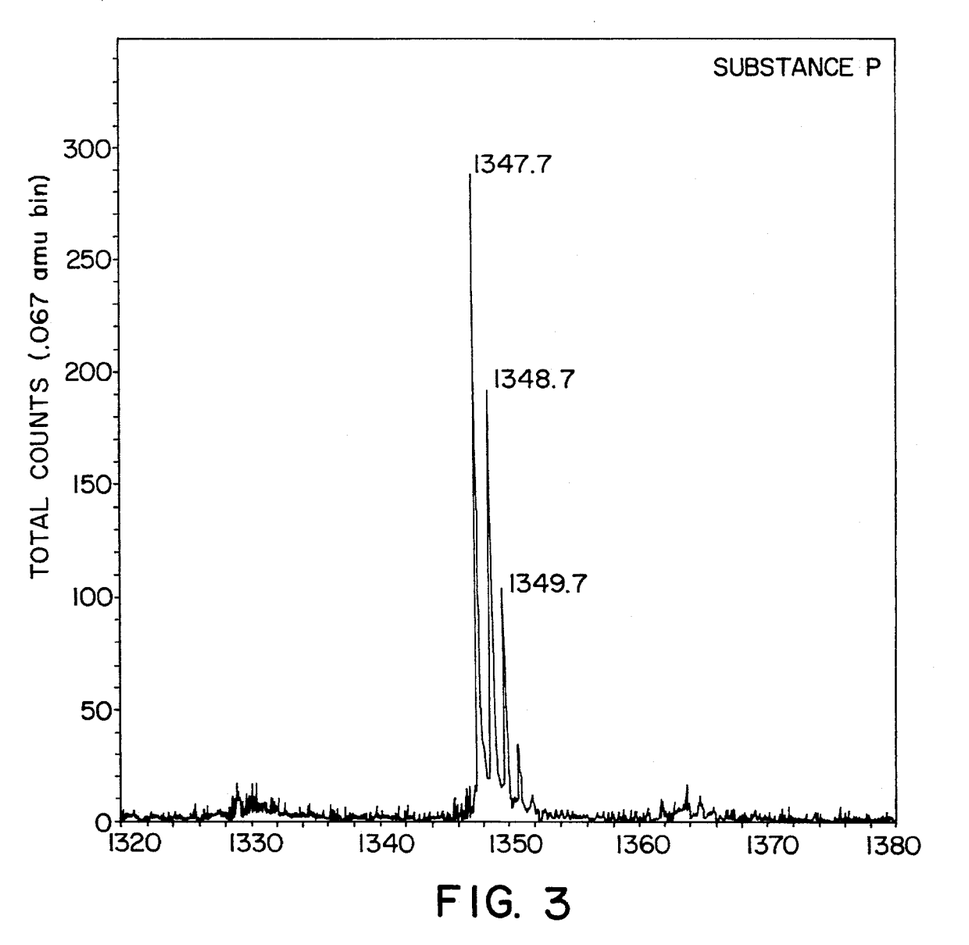
FIG. 3 is a mass spectrum of a substance P.

FIG. 3 is a TOF mass spectrum in which the matrix solution is gentisic acid and the analyte solution is substance P. Note the clear resolution of the isotopic masses at 1347.7 and 1348.7 and 1349.7 Da.

Figure 4:
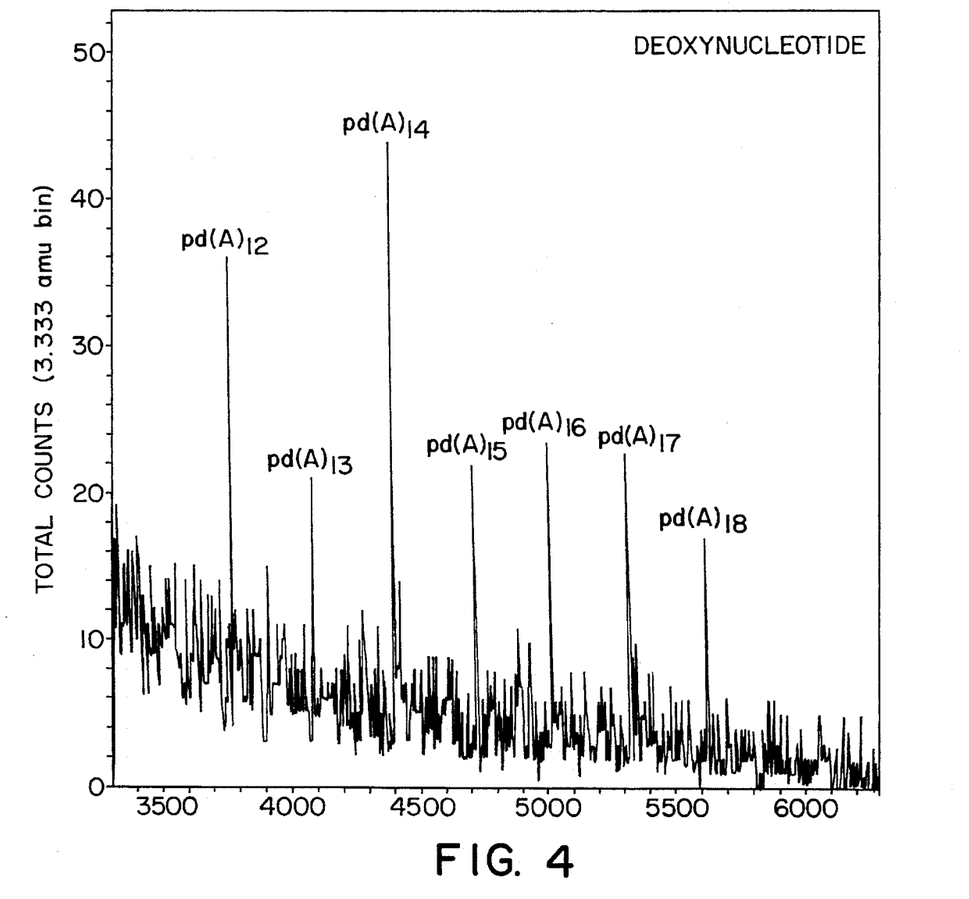
FIG. 4 is a mass spectrum of a mixture of oligo nucleotides/.

FIG. 4 is a TOF mass spectrum in which the matrix solution is 3-hydroxypicolinic acid and the analyte solution is a mixture of homooligometric deoxynucleotides poly d(A)$_{12-18}$.

Figure 5:
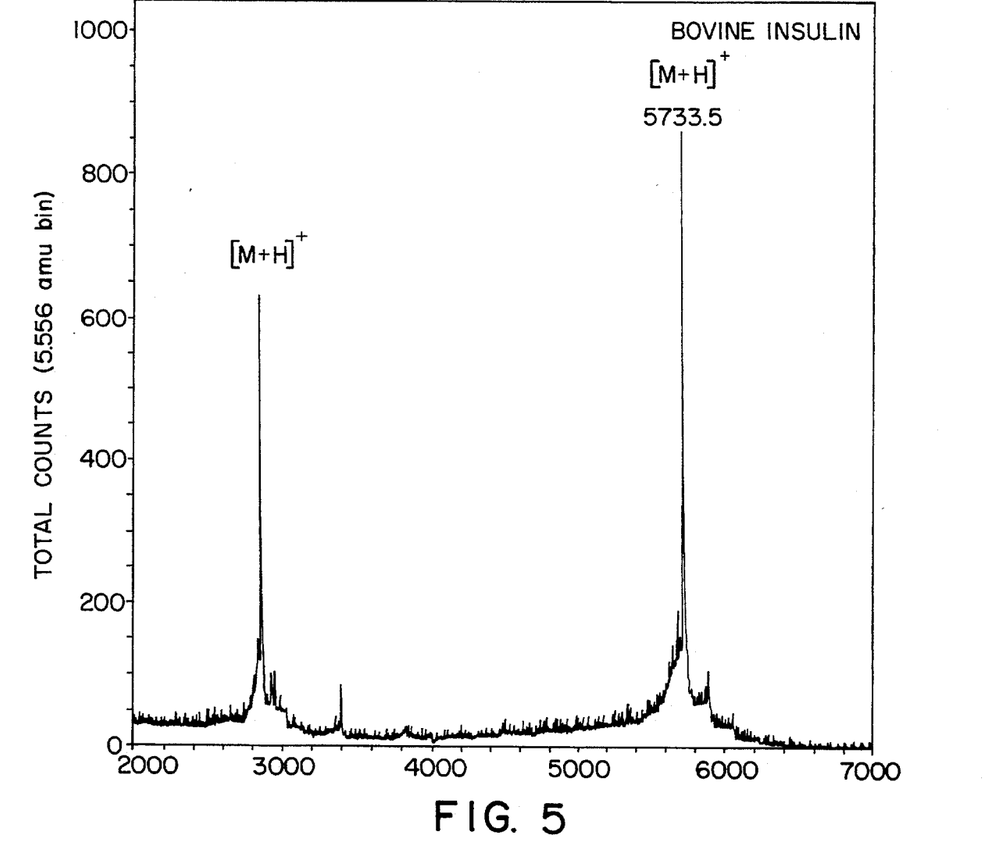
FIG. 5 is a mass spectrum of Bovine insulin.

FIG. 5 is a TOF mass spectrum in which the matrix solution is gentisic acid and the analyte solution is bovine insulin.

It is an embodiment of this invention to select a matrix forming compound for ME-SIMS applications with enhanced ability to ionize the analyte molecules. In accordance with this embodiment, the selection of the matrix forming compound is focussed on the matrix's ability to act as a compatible ionizing agent for analytes. Although we do not wish to be bound by theory, we believe that a proton donor (acid) helps in the formation of positive ions whereas a proton acceptor (base) enhances formation of negative charged analytes. Accordingly, various metallic elements including alkali metals promote positive ion formation of analytes. In addition inorganic compounds, carbon rich compounds and metallic powders which react with the analytes to promote their ionization are also effective matrix forming compounds for ME-SIMS in accordance with this invention. Photon wavelength absorption is NOT a prerequisite for selection of a ME-SIMS matrix forming compound unlike MALDI matrices which require the matrix to absorb energy. Although virtually all MALDI matrix forming compounds can be used for ME-SIMS, the reverse is not true. For example, ME-SIMS readily produces useful analyte spectra from such matrix forming compounds as pyrazine and 2-hydroxypyridine-5-carboxylic acid. These matrices do not form analyte ions by the MALDI technique because, it is believed, the fundamental mechanisms of desorption and ionization are different for ME-SIMS and MALDI processes. In addition, ME-SIMS has a much larger range of potential matrix forming compounds because it does not require photon absorption by the matrix materials.

FIG. 2 also illustrates a method of this invention for determining with improved resolution the spatial (lateral) distribution of analyte molecules on a surface. The primary beam 12 of charged particles irradiates the sample 16 consisting of analye molecules dispersed in the matrix forming compound selected in accordance with the invention. The primary beam has a beam diameter selected from the range between 0.1 to 10 micrometers. The primary beam 12 is raster scanned over the analytical surface 12 and analyte ion detection by detector 24 is synchronized to the microprobe primary beam position. Determining the lateral distribution of molecules on the surface 14 is achieved by maintaining the distribution of analyte ion signal through the mass analysis region of the instrument.

ME-SIMS data demonstrate sufficient analyte ion intensity to permit facile ion. imaging of molecules on surfaces using either ion microscope or ion microprobe techniques. The latter technique has demonstrated lateral or spatial resolutions less than 0.2 micrometers.

In accordance with the objects of this invention, a method has been disclosed for performing microanalysis of organic peptides, proteins, olignucleotides, deoxyribonucleic acid (DNA) materials and organic polymers when residues are irradiated with pulsed charged particle beams and analyzed using TOFMS techniques equipped with high precision time-to-digital converters (TDC) or transient recorders in the ion detection circuitry.

Features of the method include:

1. Sensitivity to picomolar and femtomolar levels of analyte in residue;
2. Mass resolution and mass measurement accuracies using high performance TOFMS techniques that significantly exceed capabilities of any other analysis technique employing solid residue samples and mass spectrometric detection of ions produced from the analyte;
3. Determining lateral distribution of molecules to a resolution greater than can be achieved with either MALDI or FAB.

For example, mass resolution (M/ΔM), defined as the value of detected mass divided by the full width at half maximum intensity of the peak are greater than 5,000 at a detected mass 5000 daltons (Da).

Mass measurement accuracies, defined as the $M_t-M_m/M_t * 100\%$, where $M_m$ is the measured mass value and $M_t$ is the true mass value, are typically less than 0.01% using this technique.

Lateral distribution of molecules is determined with a resolution less than one micrometer.

The method is essentially an energetic particle beam induced desorption and matrix enhanced ionization technique incorporated into a single step so that no laser is required and a broader selection of matrix materials is available. Bombardment of the solid matrix ensures stability under vacuum and under conditions that minimize sub-monolayer erosion from the ion beam. The method is characterized by low fragmentation of the analyte and is applicable to studies of masses up to at least 20,000 Da. Sample preparation is simple and rapid such as to provide fast data acquisition.

Variations and modifications of the method of this invention may be suggested by reading the specification and studying the figures which are within the scope of the invention. For example, time-of-flight mass spectrometry has been shown in the discussion of the embodiments in this specification. However, other mass spectroscopy techniques may be used instead of time-of-flight method and these modifications are within the scope of the invention. As a further example, pulses of up to two microsecond duration may be applied. The primary beam may be projected at the sample with an impact energy in a range from one hundred electron volts to three hundred million electron volts may be employed. The extraction field may have a value in a range between 0.01 and 10 volts per micrometer we therefore wish to define the scope of our invention by the appended claims.

We claim:

1. A method for measuring any one of:
   (i) a spatial distribution of a plurality of analyte particulates;
   (ii) a difference in masses of each of said plurality of analyte particulates;
   (iii) a mass of each of said analyte;
   which includes the steps in operable order:
   (a) providing a mass spectrometer constructed to project an energetic primary beam on a target surface of said mass spectrometer and to impose an accelerating field between said target surface and an accelerating electrode wherein said primary beam is one of:
      (i) an electron beam;
      (ii) a negative ion beam;
      (iii) a positive ion beam; and
      (iv) neutral beam;
   (b) mixing a quantity of an analyte component in a quantity of a matrix forming compound such as to form a sample wherein said matrix forming compound is one of an acid and a base selected to enhance ionization efficiency;
   (c) depositing said sample on a substrate;
   (d) positioning said substrate on said target surface;
   (e) projecting said primary beam onto said sample such as to sputter said analyte particulates from said sample;
   (f) directing said sputtered analyte particulates toward said accelerating electrode in an extraction field then into a drift region to a detector; and
   (g) measuring the mass-to-charge ratio of analyte said particulates by said mass spectrometer.

2. The method of claim 1 further comprising the step of determining a distribution of said analyte particulates on a sample surface, wherein,
   said step (a) includes the step of controlling said primary beam to have a beam diameter in the range 0.2 to 10 micrometer;
   said step (e) includes the step of rastering the primary beam over the sample surface; and
   said step (f) includes the step of correlating rastered position of departure of said analyte particulates from said sample with intensity and mass of analyte ions arriving at said detector such as to determine the spatial distribution of said analyte particulates on said sample substrate.

3. The method of claim 1 wherein said matrix forming compound has a component selected from the list of components which consists of said acid and said base and said step (b) includes the step of mixing a quantity of said analyte component in a quantity of said matrix forming compound such as to form said sample.

4. A method as in claim 1 wherein said step (e) includes the step of projecting said primary beam with a pulse duration in a range of pulse durations less than two microseconds.

5. A method as in claim 1 wherein said step (e) includes the step of projecting said primary beam with a pulse repetition frequency in a range between one hundred and one hundred thousand Hz.

6. A method as in claim 1 wherein said step (e) includes the step of projecting said primary beam with a maximum particle dosage in a range of greater than $10^{15}$ particles per $cm^2$.

7. The method of claim 1 wherein said step (e) includes the step of projecting said primary beam at said sample with an impact energy in a range from one hundred electron volts to three hundred million electron volts.

8. A method as in claim 1 wherein said step (f) includes the step of directing said sputtered analyte particulates toward said accelerating electrode in said extraction field having a value in a range between 0.01 and 10 volts per micrometer.

9. A method as in claim 1 wherein said detector is an ion detector and said step (g) includes the step of directing said analyte particulates toward said ion detector.

10. A method as in claim 1 wherein said step (g) includes the step of measuring rate of arrival at said detector vs. drift time of said analyte particulates using detector electronic means having one of a time-to-digital converter means and a transient recorder means.

11. The method of claim 1 wherein said steps (b) and (c) include the steps:
 (i) dissolving a non-volatile analyte component in one of an organic solvent and an inorganic solvent to produce an analyte solution;
 (ii) dissolving said matrix forming compound in another one of an organic solvent and an inorganic solvent to produce a matrix solution;
 (iii) mixing said analyte and matrix solutions to form a sample solution such that analyte to matrix molecular concentration ratio in said sample solution has a range between 1 to $10^{-5}$;
 (iv) depositing a sample quantity of said sample solution on said substrate; and
 (v) drying said sample quantity deposited on said substrate.

12. The method of claim 11 wherein said step (iv) includes the step of depositing said sample quantity on said substrate, said substrate being selected from a group of substrates consisting of metals, semiconductors and insulators.

13. The method of claim 12 wherein said nonvolatile analyte component is selected from a group which consists of peptides, proteins, olignucleotides, deoxyribonucleic acid and organic polymers.

14. The method of claim 11 wherein said matrix forming compound is selected from a group which consists of an organic acid, an organic base, an inorganic acid, an inorganic base and metallic powders.

15. The method of claim 11 wherein said one of an inorganic solvent and an organic solvent is selected from a group that consists of water, acetonitrile, alcohol, acetone, acid, benzene, ether, chloroform, pyridine, and aqueous alkaline solutions.

16. The method of claim 11 wherein said matrix forming compound has a molecular weight in the range between 100 to 1000 Da.

17. The method of claim 11 wherein said analyte component has a molecular weight in the range up to 20,000 Da.

18. The method of claim 1 wherein a resolution of said spatial distribution is less than one micrometer.

19. A method for measuring one of:
 (i) a spatial distribution of a plurality of analyte particulates at lateral resolutions in a range less than one micrometer;
 (ii) a difference in masses of each of said plurality of analyte particulates at a mass resolution in a range greater than five thousand at a detected mass of greater than five thousand Daltons; and
 (iii) a mass of each of said analyte particulates measured to a precision that is smaller than 0.01%.;
which includes the steps in operable order:
 (a) providing a mass spectrometer constructed to project an energetic primary beam on a target surface of said mass spectrometer and to impose an accelerating field between said target surface and an accelerating electrode wherein said primary beam is one of:
  (i) an electron beam;
  (ii) a negative ion beam;
  (iii) a positive ion beam; and
  (iv) a neutral beam;
 (b) mixing a quantity of an analyte component in a quantity of a matrix component such as to form a sample in which the ratio of the molecular concentration of said analyte component to said matrix component is in a range between 1 to $10^{-5}$ and in which said matrix forming component has a molecular weight between 100 and 1000 Da.;
 (c) depositing said sample on a substrate whereby analyte particulates are deposited on said substrate;
 (d) positioning said substrate on said target surface;
 (e) projecting said primary beam onto said sample such as to sputter said analyte particulates from said substrate wherein said primary beam:
  (i) has a pulse duration in a range less than two microseconds;
  (ii) has a pulse repetition frequency in a range between one hundred and one hundred thousand Hz.;
  (iii) has a maximum particle dosage in a range of greater than $10^{15}$ particles per $cm^2$;
 (f) directing said sputtered analyte particulates toward said accelerating electrode in an extraction field then into a drift region to a planar detector wherein said extraction field has a value in a range between 0.01 and 10 volts per micrometer; and
 (g) measuring rate of arrival at said detector vs. drift time of said analyte particulates using detector electronic means having one of a time-to-digital converter and a transient recorder.

20. A method for measuring any one of:
 (i) a spatial distribution of a plurality of ionized particulates of an analyte wherein each said particulate is at least one analyte molecule;
 (ii) a difference in masses of each of said plurality of ionized particulates of analyte; and
 (iii) a mass of each of said ionized particulates of analyte;
wherein positive ionized particulates of said analyte are ejected when said analyte is bombarded by a primary beam of energetic particles, which includes the steps in operable order:
 (a) providing a mass spectrometer constructed to project an energetic primary beam on a target surface of said mass spectrometer and to impose an accelerating field between said target surface and an accelerating electrode;
 (b) mixing a quantity of said analyte in a quantity of a matrix forming component containing proton donors such as to form a sample;
 (c) depositing said sample on a substrate;
 (d) positioning said substrate on said target surface;
 (e) projecting said primary beam onto said sample such as to eject said ionized particulates of analyte from said substrate;
 (f) directing said ejected ionized particulates of analyte toward said accelerating electrode in an extraction field then through said mass spectrometer, and (g) using said mass spectrometer having a detector electronic means and an ion detector to measure masses of said ejected ionized particulates of analyte.

21. The method of claim 20 wherein said step (b) comprises the step of mixing a quantity of said analyte in a quantity of a matrix forming component containing a metal.

22. The method of claim 21 wherein said metal is an alkali.

23. The method of claim 20 wherein said step (b) comprises the step of mixing a quantity of said analyte in a quantity of a matrix forming component containing a base.

24. A method for measuring any one of:
(i) a spatial distribution of a plurality of ionized particulates of analyte;
(ii) a difference in masses of each of said plurality of ionized particulates of analyte; and
(iii) a mass of each of said ionized particulates of analyte;
wherein ionized particulates of said analyte are ejected when said analyte is bombarded by an energetic primary beam of negative particles, which includes the steps in operable order:
(a) providing a mass spectrometer constructed to project an energetic primary beam on a target surface of said mass spectrometer and to impose an accelerating field between said target surface and an accelerating electrode wherein said primary beam is a negative ion beam;
(b) mixing a quantity of said analyte in a quantity of a matrix forming component containing proton acceptors such as to form a sample;
(c) depositing said sample on a substrate;
(d) positioning said substrate on said target surface;
(e) projecting said primary beam onto said sample such as to eject said particulates of analyte from said substrate;
(f) directing said ejected ionized particulates of analyte toward said accelerating electrode in an extraction field then through said mass spectrometer; and
(g) using said mass spectrometer having a detector electronic means and an ion detector to measure masses of said ejected analyte ions.

25. The method of claim 24 further comprising the step of determining a distribution of said analyte particulates on a sample surface, wherein, said step (a) includes the step of controlling said primary beam to have a beam diameter in the range 0.2 to 10 micrometer;

said step (e) includes the step of rastering the primary beam over the sample surface; and said step (f) includes the step of correlating rastered position of departure of said analyte from said sample with intensity and mass of said analyte arriving at said detector such as to determine the spatial distribution of said analyte particulates on said sample.

* * * * *